United States Patent [19]

Cassidy

[11] Patent Number: 4,569,237

[45] Date of Patent: Feb. 11, 1986

[54] METHOD OF SAMPLING MOLTEN METAL

[75] Inventor: John E. Cassidy, Churchville, Pa.

[73] Assignee: Electro-Nite Co., Philadelphia, Pa.

[21] Appl. No.: 600,613

[22] Filed: Apr. 16, 1984

[51] Int. Cl.$^4$ .............................................. G01N 1/12
[52] U.S. Cl. .................................................. 73/864.58
[58] Field of Search ......... 73/864.58, DIG. 9, 864.53, 73/864.54, 864.55, 864.56, 864.57, 864.59; 249/DIG. 4

[56] References Cited

U.S. PATENT DOCUMENTS

| | | | |
|---|---|---|---|
| 3,481,201 | 12/1969 | Falk | 73/DIG. 9 |
| 3,534,614 | 10/1970 | Creswell | 73/864.58 X |
| 3,559,452 | 2/1971 | Perbix et al. | 73/DIG. 9 |
| 3,565,606 | 2/1971 | Carlson et al. | 73/DIG. 9 |
| 3,572,124 | 3/1971 | Naguoka et al. | 73/DIG. 9 |
| 3,681,972 | 8/1972 | Mahanty et al. | 73/DIG. 9 |
| 3,685,359 | 8/1972 | Boron et al. | 73/DIG. 9 |
| 3,704,621 | 12/1972 | Zickefoose et al. | 73/864.58 |
| 3,766,772 | 10/1973 | Kern et al. | 73/DIG. 9 |
| 3,824,837 | 7/1974 | Naguoka et al. | 73/DIG. 9 |
| 3,996,803 | 12/1976 | Falk | 73/864.58 X |
| 4,067,242 | 1/1978 | Judge | 73/864.58 |
| 4,125,024 | 11/1978 | Vierbiecky | 73/864.58 X |
| 4,438,653 | 3/1984 | Beentjes | 73/DIG. 9 |

Primary Examiner—Stewart J. Levy
Assistant Examiner—Tom Noland
Attorney, Agent, or Firm—Seidel, Gonda, Goldhammer & Abbott

[57] ABSTRACT

Molten metal is sampled by immersing a lance into a bath. The lance includes a chamber having a deoxidant. Two sets of lances are disclosed with the amount of deoxidant being different in each set. One set of lances is used during in-blow operation and the other is used during blow-interrupt operation.

7 Claims, 2 Drawing Figures

METHOD OF SAMPLING MOLTEN METAL

BACKGROUND OF THE INVENTION

Devices for immersion into a bath of molten ferrous metal to retrieve a sample and methods of using the same are known. A typical device includes an expendable probe having a chamber which is adapted to be filled with the molten metal after a protective layer over an inlet to the chamber is consumed by the bath. In the chamber it is necessary to provide a deoxidant. The amount of deoxidant varies from manufacturer to manufacturer over the range of about 0.2–1% by weight of the sample and steel grades.

Most steel manufacturers use two such devices per heat. Some steel manufacturers take a first sample in an oxygen furnance during in-blow, namely when oxygen is being blown into the molten metal. Other manufacturers take the first sample during a time known as blow-interrupt, that is, after blowing of oxygen has ceased. The second sample is taken at the end of the heat to verify predicted results. Testing of commerically available sampling devices at each of said time periods shows erratic results with respect to quality of samples and/or the quality of carbon readings.

Quality of samples refers to the lack of pin holes or other undesirable features. Carbon readings are reflected by a cooling curve which is monitored by a computer correlated with a desired cooling curve. Poor quality carbon readings are those which deviate from the desired cooling curve by more than 1.5° C.

The present invention is directed to a solution of a problem of how to sample molten metal and obtain a reliable carbon reading and good samples.

SUMMARY OF THE INVENTION

In accordance with the present invention, there is disclosed a method of sampling ferrous molten metal. The method is practiced by having first and second sets of immersion probes with each probe having a sampling chamber containing a deoxidant. The first set of probes has a substantially smaller amount of deoxidant than the second set of probes. A probe of the first set is utilized for obtaining a sample only during in-blow operation while a probe of the second set is used only during blow-interrupt.

It is an object of the present invention to provide a novel method for sampling molten metal either during blow-interrupt or during in-blow operation in a manner which is simple and reliable with respect to quality of the samples and quality of carbon readings.

Other objects will appear hereinafter.

For the purpose of illustrating the invention, there is shown in the drawings a form which is presently preferred; it being understood, however, that this invention is not limited to the precise arrangements and instrumentalities shown.

DETAILED DESCRIPTION

Figure 1:
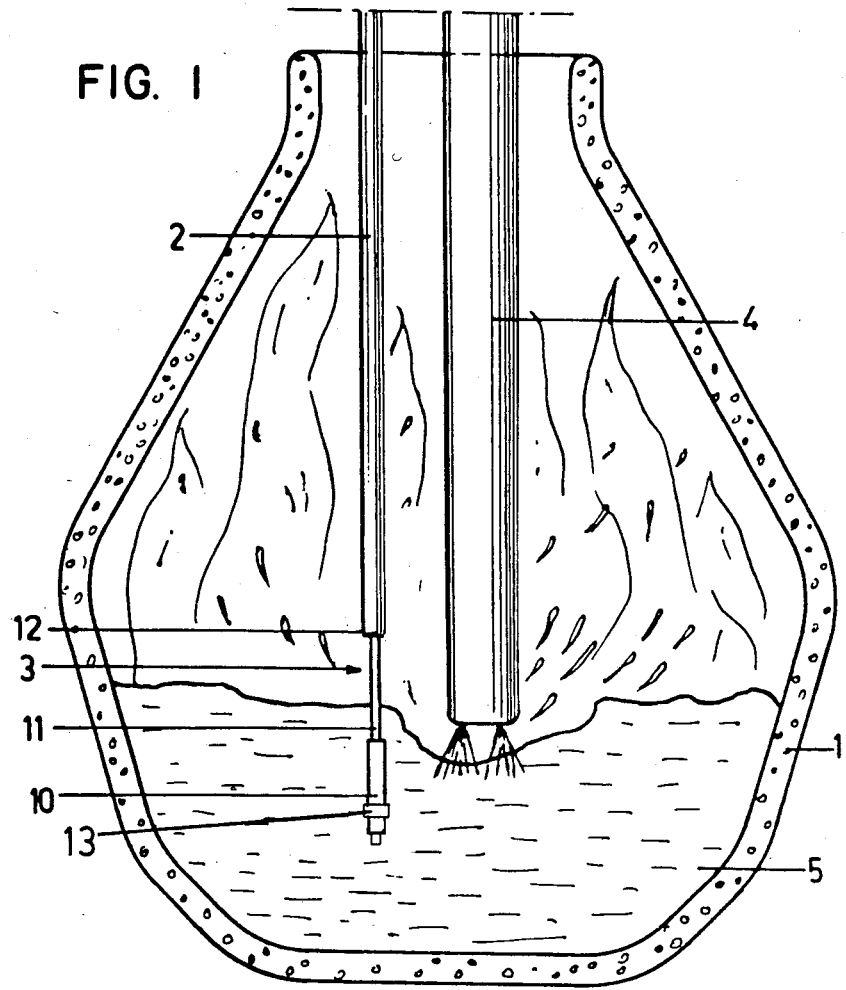
FIG. 1 is a diagrammatic sectional view of an oxygen furnance with a probe immersed in the molten metal.
Figure 2:
FIG. 2 is an elevation view of an alternative probe with respect to the probe shown in FIG. 1.

Referring to the drawing in detail, wherein like numerals indicate like elements, there is shown in FIG. 1 a basic oxygen furnance designated generally as 1 and containing a body of molten metal such as steel and designated generally as 5. A lance 2 and the oxygen tube 4 extend into the furnance 1.

A probe designated generally as 3 is removably attached to the lower end of the lance 2 at the joint 12.

The probe 3 includes a reduced diameter portion attached to the lance and enlarged diameter portion 10 containing a sampling chamber. Access to the sampling chamber is by way of a port which is temporarily closed by sleeve 13. Sleeve 13 is made from a material which is readily consumed by the bath of molten metal 5 to thereby facilitate entry of molten metal into the sampling chamber.

As diagramatically illustrated in FIG. 1, blowing of oxygen into the molten metal 5 produces a violent reaction at the surface of the molten metal. Hence, FIG. 1 represents the in-blow time period and sampling of the molten metal would be by way of probe 3. During blow-interrupt, sampling is by way of probe 3'. Probe 3' is identical with probe 3 except that the amount of deoxidant in the sampling chamber is different. For in-blow operation, the probe 3 preferably has about 0.3% of deoxidant by weight of the sample. For blow-interrupt operation, probe 3' has a deoxidant in the amount of about 0.7% by weight of the sample. A wide variety of deoxidants may be utilized. The preferred deoxidant is aluminum in strip or wire form.

The amount of deoxidant is generally a function of the oxygen content of the molten metal. Since the oxygen is no longer being blown into the molten metal 5 during the blow-interrupt time period, it would be logical to assume that the amount of deoxidant would be the same or less than that utilized during in-blow operation. However, it has been found that the amount of deoxidant during blow-interrupt operations should be double the amount used during in-blow operation. It is believed that the reason for that relationship is as follows. During blow-interrupt, slag forms on the surface of the molten metal and acts as a blanket to prevent the escape of oxygen. During in-blow operation, the oxygen is free to escape through the surface of the molten metal.

Test results with respect to quality of the sample and using commercially available probes are as follows:

| Type Probes | % Alum | No. Heats | % Good Samples |
| --- | --- | --- | --- |
| | | In-blow | |
| A | 0.7 | 12 | 81.8 |
| B | 0.50 | 58 | 87.3 |
| C | 0.3 | 64 | 94.6 |
| D | 0.3 | 85 | 96.3 |
| E | 0.3 | 55 | 90.9 |
| F | 0.3 | 67 | 96.8 |
| G | 0.5 | 119 | 78.2 |
| | | Blow-Interrupt | |
| A | 0.7 | 174 | 97.1 |
| B | 0.50 | 616 | 80.1 |
| H | 0.3 | 52 | 79.6 |
| F | 0.3 | 100 | 76 |

As reflected by the in-blow test results, the best quality samples were obtained when the percentage of deoxidant was 0.3% by weight. During blow-interrupt, the best quality samples were obtained when the percentage of deoxidant was 0.7% by weight.

Test results with respect to good carbon readings are as follows:

| Type Probe | % Alum | No. Heats | % Good C |
|---|---|---|---|
| In-blow | | | |
| H | 0.3 | 16 | 100 |
| F | 0.3 | 67 | 95.4 |
| B | 0.50 | 58 | 82.5 |
| A | 0.405 | 12 | 83.3 |
| Blow-Interrupt | | | |
| H | 0.3 | 52 | 92.1 |
| F | 0.3 | 100 | 90.9 |
| B | 0.50 | 616 | 93.3 |
| A | 0.405 | 185 | 93.3 |

It will be noted that during in-blow, the best carbon readings were in connection with probes having 0.3% deoxidant by weight. During blow-interrupt, the best carbon readings were obtained when the percent deoxidant was b 0.4% by weight.

Thus, the present invention recognizes the need for two different types of probes having different amounts of deoxidant depending upon the time in which they are being used. During in-blow, the amount of deoxidant should be about 0.3% by weight and during blow-interrupt, the amount of deoxidant should be at a higher figure such as 0.7%. By following this simple relationship, the percentage of good quality samples and good carbon readings can be increased as reflected by the above test results.

The present invention may be embodied in other specific forms without departing from the spirit or essential attributes thereof and, accordingly, reference should be made to the appended claims, rather than to the foregoing specification, as indicating the scope of the invention.

I claim:

1. A method of sampling molten metal comprising the steps of:
   (a) providing first and second models of immersion probes each having a sampling chamber,
   (b) taking a first sample by immersing the first probe having a predetermined amount of deoxidant by weight of the sample in the chamber into a bath of molten metal while oxygen is being blown into the molten metal, and
   (c) compensating for the apparent increase in oxygen in the bath of molten metal after blowing of oxygen has ceased by using the second probe having at least about twice the amount of deoxidant by weight of the sample in the chamber as the amount of deoxidant in the chamber of the first probe to take a second sample.

2. The method in accordance with claim 1 including using a deoxidant in the sampling chamber of the first probe in an amount of about 0.3% by weight of the sample and using a deoxidant in the sampling chamber of the second probe in an amount of about 0.7% by weight of the sample.

3. The method in accordance with claim 2 including using probes having the same size sampling chamber.

4. The method in accordance with claim 1 wherein the second sample is taken at the end of the heat to verify predicted results.

5. A kit of probes for sampling molten metal comprising first and second models of immersion probes each probe having a sampling chamber containing deoxidant therein, at least one probe of each model in the kit, the sampling chamber of each second model probe having at least about twice the amount of deoxidant by weight of the sample as the amount of deoxidant by weight in the chamber of each first model probe, whereby the first probe is to be used only to sample molten metal when oxygen is being blown into the molten metal and the second probe is to be used only to sample the molten metal after the blowing of oxygen has ceased.

6. The kit in accordance with claim 5 wherein the deoxidant in the sampling chamber in each first model probe is in an amount of about 0.3% by weight of the sample and the deoxidant in each second model is in an amount of about 0.7% by weight of the sample.

7. The kit in accordance with claim 5 wherein the sampling chambers of the first and second probes are the same size.

* * * * *